United States Patent [19]
Berens

[11] Patent Number: 5,323,795
[45] Date of Patent: Jun. 28, 1994

[54] DENTAL INSTRUMENT FOR MASSAGING GUMS AND CLEANING TEETH

[76] Inventor: Mathew G. Berens, 8272 Honeytree Blvd., Canton, Mich. 48187

[21] Appl. No.: 147,623

[22] Filed: Nov. 5, 1993

[51] Int. Cl.$^5$ ............................................. A45D 44/18
[52] U.S. Cl. ..................... 132/309; 15/110; 601/139
[58] Field of Search ............... 132/308, 309, 321, 329; 433/141, 142; 128/62 A; 15/110

[56] References Cited

U.S. PATENT DOCUMENTS

| | | | |
|---|---|---|---|
| D. 296,271 | 6/1988 | Kobayashi | D4/108 |
| 2,016,597 | 10/1935 | Drake | 128/62 A |
| 2,083,595 | 6/1937 | Clarren | 128/62 A |
| 2,141,969 | 12/1938 | Benz | 15/110 |
| 2,788,000 | 4/1957 | Lather et al. | 128/62 A |
| 2,800,899 | 7/1957 | Barron | 128/62 A |
| 2,888,008 | 5/1959 | Rosenthal | 132/309 |
| 4,486,109 | 12/1984 | Rosofsky | 401/24 |
| 4,879,781 | 11/1989 | Desimone | 15/110 |

OTHER PUBLICATIONS

Butler Toothbrush Product of J. O. Butler Co., Chicago, Ill., date unknown.
Tooth Stain Eraser Product of Ranir/DCP Corp., Grand Rapids, Mich., date unknown.

Primary Examiner—Cary E. O'Connor
Attorney, Agent, or Firm—Peter D. Keefe

[57] ABSTRACT

A dental instrument, particularly such an instrument equipped on a toothbrush, which provides excellent tooth picking function, gum line probing, and gum massage. A distal end segment of a handle is provided with an elastomer oral hygiene member in the form of both a toothpick and a gum massager. An arm of planar shape that is elongated along the handle axis and tapering to an edge remote from the handle, projects perpendicularly from the distal end segment of the handle. The oral hygiene member is formed over the distal end segment of the handle, inclusive of the arm. The oral hygiene member provides a gum massager, having preferably a convex dome shape, wherein the center of curvature thereof is located axially with respect to the handle. The oral hygiene member further provides a toothpick of planar shape formed over the arm. The toothpick is elongated along the handle axis and tapers to a tip radially remote from the arm. The taper of the toothpick and the arm, together with the radial length of the arm in relation to the radial length of the toothpick provides a progressive variation in flexibility of the toothpick, with greatest flexibility at the tip, and least flexibility adjacent the distal end segment of the handle. A handle indentation accommodates the toothpick, thereby allowing its passage through a conventional toothpick holder aperture.

19 Claims, 1 Drawing Sheet

DENTAL INSTRUMENT FOR MASSAGING GUMS AND CLEANING TEETH

BACKGROUND OF THE INVENTION

1. Field of the Invention

The present invention relates to dental instruments for picking teeth and massaging gums. Still more particularly, the present invention relates to a tooth brush having a handle wherein the end thereof is provided with an oral hygiene member having a tapered, variably flexible tooth pick and an adjacent gum massager.

2. Description of the Related Art

It is well known that for proper oral hygiene, the teeth and adjacent gum tissues must be maintained clean. Further, in order for the gums to be healthy, it is important to provide massage stimulation thereto in order to promote blood circulation, improve tissue softness and suppleness, and encourage the gums not to recede.

For persons suffering from dental disease, such as gingivitis and periodontal disease, it is very important to maintain a strict regiment of tooth and gum care in order to arrest further effects of the disease and promote healing. However, in order for an individual to be able to effectively and conveniently accomplish such a regimen it is necessary to use exactly the proper dental instrument therefor.

Although an individual may use his or her finger as a gum massager, this is not desirable. There are several reasons for this. Firstly, there is too great a danger that the individual's finger nail will accidentally abrade the gum tissue, thereby introducing additional gum tissue injury and further potential for infection. Secondly, the finger used (usually the index finger) is, for many people too large to effectively massage gum tissue. Thirdly, an individual's fingers are generally too contaminated with infectious substances to be safely placed in the mouth on a regular basis. Thus, it is impractical, unwise and unsafe for an individual to use a finger to massage his or her gums. Accordingly, a dental instrument is needed which facilitates gum massage without any of the problems associated with finger usage.

U.S. Design 296,271 discloses an example of a class of toothbrush in which the distal end of the handle is provided with a cone shaped dental pick constructed of an elastomer material such as rubber. Such cones project perpendicularly with respect to a flat side of the handle and are typically about one-half inch in length. This dimensional relationship is bulky and makes handling of the toothbrush handle awkward for brushing and limits movements of the cone within the mouth to adequately pick between teeth and probe the gum line, especially when the tongue and the cheek are involved in accessing these locations.

The cone shaped dental pick is not well suited to penetrate between teeth, since the apex portion of the cone is so flexible that it is unable to provide sufficient mechanical support for the tip to penetrate in an effective and useful manner unless the tip is precisely aligned at ninety degrees to the selected space between the teeth. This alignment requirement can result in great frustration for the user to attain, especially because of the aforementioned bulk associated with the handle and cone structure.

While the cone and handle structure can be used to probe between teeth and at the gum line, an additional disadvantage to this cone and handle structure is its inability to properly massage the gums. When using the cone for this purpose, the smallness of the apex of the cone serves to confine its gum contact to very localized portions of the gum which may result in irritation or injury to the gum tissue, especially if it is already inflamed.

A further disadvantage of the cone and handle structure is associated with the fact that there is insufficient clearance to keep the handle from contacting the lip area when the cone is used around the front side of the teeth, or the lower teeth area when the cone is used around the back side of the teeth.

Yet another disadvantage of the cone and handle structure is associated with the fact that since the cone projects outwardly from the flat side of the handle, the aperture of conventional toothbrush holders which are pre-sized to accommodate toothbrush handles, cannot accommodate the handle with the cone. Therefore, users frequently place their cone equipped toothbrushes on unsanitary surfaces, thereby enhancing their risk of oral infection.

Accordingly, what is needed is a dental instrument, particularly such an instrument equipped on a toothbrush, which provides excellent tooth picking function, gum line probing, and gum massage.

SUMMARY OF THE INVENTION

The present invention is a dental instrument, particularly such an instrument equipped on a toothbrush, which provides excellent tooth picking function, gum line probing, and gum massage.

The dental instrument according to the present invention is composed of a handle having a post-like distal end segment. The distal end segment is provided with an elastomer oral hygiene member in the form of both a toothpick and a gum massager. In this regard, the distal end segment of the handle is provided with a reduced diameter, thereby providing an abutment for sealably interfacing the handle with the elastomer material of the oral hygiene member. An arm of planar shape that is elongated along the handle axis and tapering to an edge remote from the handle, projects perpendicularly from the distal end segment of the handle. The oral hygiene member is formed over the distal end segment of the handle, inclusive of the arm.

The oral hygiene member provides a gum massager, having preferably a convex dome shape, wherein the center of curvature thereof is located axially with respect to the handle. The gum massager has a radius of curvature which provides distribution of contact force onto a wide area of the gum, thereby preventing injury thereto, and further providing gentle and safe massage to presently inflamed areas.

The oral hygiene member further provides a toothpick of planar shape formed over the arm. The toothpick is elongated along the handle axis and tapers to a tip radially remote from the arm. Preferably, the length of the arm, as measured to the edge thereof, is approximately sixty percent the length of the toothpick, as measured to the tip thereof. The taper of the toothpick and the arm, together with the radial length of the arm in relation to the radial length of the toothpick provides a progressive variation in flexibility of the toothpick, with greatest flexibility at the tip, and least flexibility adjacent the distal end segment of the handle. Further, the longitudinal length of the toothpick and the longitudinal length of the arm is preselected to provide mechanical strength for the tip to allow the toothpick to easily and effectively pick teeth and effectively probe the gum line.

When the dental instrument is connected with a toothbrush, the handle is provided with a reduced diameter along a transverse axis that is perpendicular with respect to the bristles of the brush of the toothbrush, thereby forming a handle indentation. The arm and toothpick project radially along the transverse axis. In this regard, preferably the length of the tip approximates the length of the handle indentation, thereby allowing the toothbrush to be easily and effectively handled when using the brush thereof or the dental instrument thereof, and further allowing the handle with the oral hygiene member to fit easily into the aperture of a conventional toothbrush holder.

These, and additional objects, advantages, features and benefits of the present invention will become apparent from the following specification.

DETAILED DESCRIPTION OF THE PREFERRED EMBODIMENT

Figure 1:
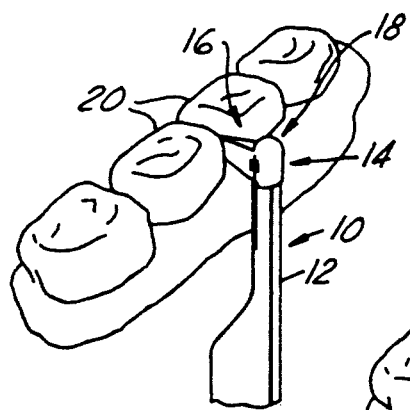
FIG. 1 is a perspective depiction of the dental instrument according to the present invention, shown in operation picking teeth.
Figure 2:
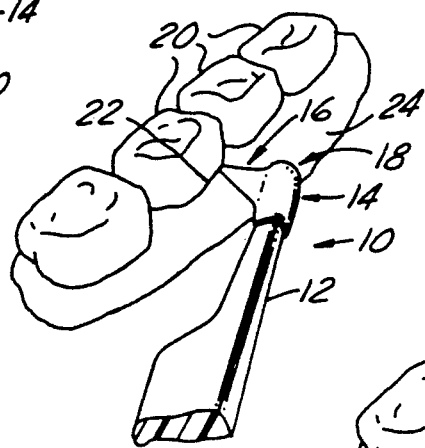
FIG. 2 is a perspective depiction of the dental instrument according to the present invention, shown in operation probing a gum line.
Figure 3:
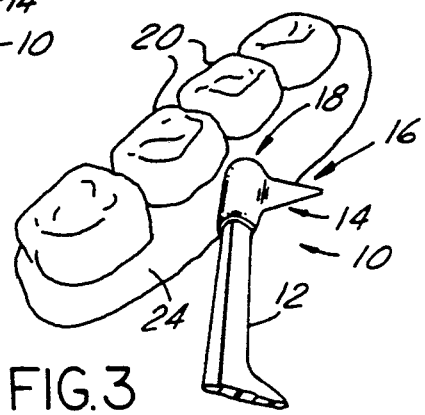
FIG. 3 is a perspective depiction of the dental instrument according to the present invention, shown in operation massaging gums.
Figure 7:
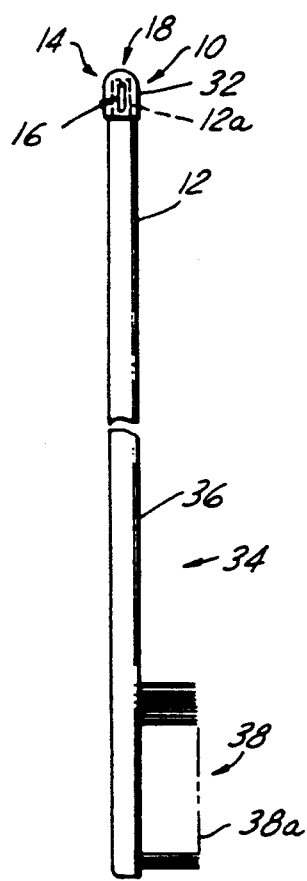
FIG. 7 is a side view of a toothbrush equipped with the dental instrument according to the present invention.
Figure 8:
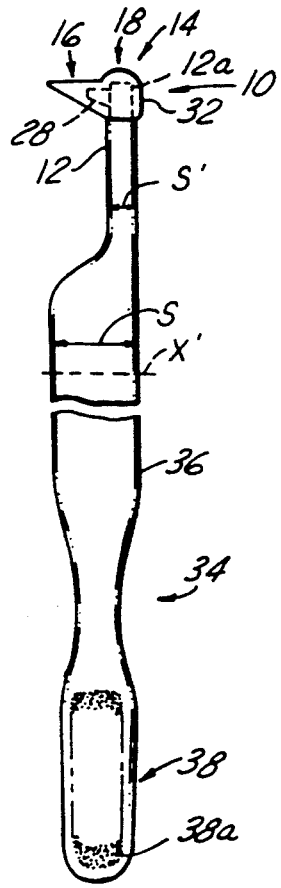
FIG. 8 is a front view of the toothbrush equipped with the dental instrument shown in FIG. 7.
Figure 5:
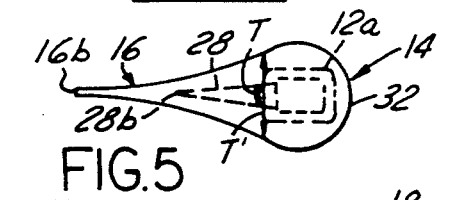
FIG. 5 is a top plan view of the dental instrument according to the present invention.
Figure 4:
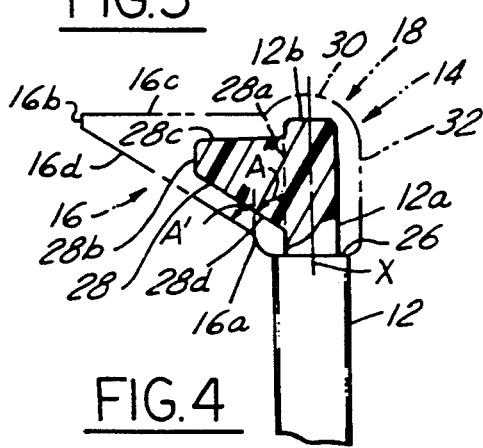
FIG. 4 is a detail, partly sectional side view of the dental instrument according to the present invention.

FIGS. 1 through 3 show the dental instrument 10 according to the present invention in a variety of uses not heretofor possible in one device. It will be seen that the dental instrument 10 includes a handle 12 having a post-like distal end segment 12a to which is connected an oral hygiene member 14. The oral hygiene member 14 provides a toothpick 16 and a gum massager 18. FIG. 1 shows the toothpick 16 of the dental instrument 10 picking between teeth 20. FIG. 2 shows the toothpick 16 of the dental instrument 10 being used to probe the gum line 22 between teeth 20 and gums 24. Finally, FIG. 3 shows the gum massager 18 of the dental instrument 10 massaging gums 24. The structure and function of the dental instrument 10 for providing the aforementioned uses will now be detailed with reference being had to FIGS. 4 and 5.

The handle 12 is constructed of a preferably rigid and noncorrodible material, such as plastic. The handle 12 has a first predetermined cross-section and the distal end segment 12a of the handle 12 is provided with a reduced cross-section, wherein an abutment 26 is formed at the interface of the aforesaid two cross-sections. The oral hygiene member 14 is located at the distal end segment 12a of the handle 12.

An arm 28 of planar shape projects perpendicularly with respect to the handle axis X of the handle 12 from the distal end segment 12a thereof. The arm 28 is composed of a flexible material whose flexibility depends upon its thickness, preferably plastic. Preferably, the arm 28 is formed integrally with the handle 12 (both being constructed of plastic). The arm 28 is elongated along the handle axis X and is further tapered, ranging from a maximum thickness T its base 28a whereat it connects with the handle 12 progressively to a minimum thickness at an edge 28b. The taper of the arm 28 gives it progressively greater resistance to flexing from the edge 28b to the base 28a. The preferred shape of the arm 28 is defined by a trailing side 28c which is oriented perpendicular with respect to the handle axis X and an opposite leading side 28d which is oriented at an acute angle A of preferably approximately seventy-five degrees with respect to the handle axis X, wherein the edge 28b has a longitudinal length that is approximately one-half the longitudinal length of the base 28a. Preferably, the base 28a is situated approximately medially with respect to the abutment 26 and the terminus 12b of the distal end segment 12a.

The oral hygiene member 14 is composed of an elastomer material, such as soft rubber, that is formed over the distal end segment 12a of the handle 12, inclusive of the arm 28. The oral hygiene member 14 includes the toothpick 16 and the gum massager 18. The elastomer material seals against the abutment 26 and envelops the distal end segment 12a, inclusive of the arm 28.

The toothpick 16 is planar shaped similarly to the arm 28, which is coincidentally situate entirely thereinside. In this regard, the toothpick 16 is elongated along the handle axis X and is further tapered, ranging from the maximum thickness T' at its base 16a, progressively to minimum thickness at its tip 16b. The taper of the toothpick 16 gives it progressively greater resistance to flexing from the tip 16b to its base 16a. The preferred shape of the toothpick 16 is defined by a trailing side 16c which is oriented perpendicular with respect to the handle axis X and an opposite leading side 16d which is oriented at an acute angle A' of preferably approximately seventy-five degrees with respect to the handle axis X, wherein the tip 16b has a longitudinal length that is on the order of approximately one-seventh the longitudinal length of the base 16a. The longitudinal length of the toothpick 16 and the arm 28 along the handle axis X is preselected to provide mechanical strength for the tip 16b so as to allow the toothpick to easily and effectively pick between teeth 20 and, further, to effectively probe the gum line 22.

The gum massager 18 is preferably characterized by a convex dome 30 located at the terminus 12b of the distal end segment 12a, having a center of curvature on the handle axis X. The radius of curvature of the convex dome 30 is sufficiently large to present a wide area of contact with the user's gums 24 so as to promote massage induced healing and tissue health, without involvement of injury to inflamed gum tissue, as would occur in the case of usage of a conventional cone. Further, the sidewall 32 of the oral hygiene member 14 further serves as additional gum massage surfaces of the gum massager 18. The base 16a of the toothpick 16 is connected integrally with the sidewall 32.

Figure 6:
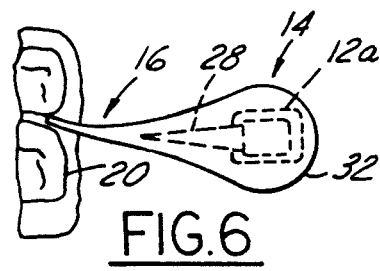
FIG. 6 is a top plan view of the dental instrument according to the present invention, shown flexing in response to contact with a tooth.

As can be seen at FIG. 6, the flexibility of the toothpick 16 is moderated by the arm 28 to thereby provide a predetermined degree of flexibility which varies from being most flexible at the tip 16b to being essentially inflexible at the base 16a. The taper of the toothpick 16 and the arm 28, together with the radial length of the trailing side 28c of the arm in relation to the radial length of the trailing side 16c of the toothpick is preselected (the radial length of the trailing side 28c of the arm 28 being preferably on the order of sixty percent the radial length of the trailing side 16c of the toothpick) to provide a progressive variation in flexibility of the toothpick, with greatest flexibility being located at the tip 16b and least flexibility being located at the base 16a. Further, the longitudinal length of the toothpick 16, varying from that of the tip 16b to that of its base 16a, and the longitudinal length of the arm 28, varying from that of the edge 28b to that of its base 28a, is preselected to provide mechanical strength for the tip of the toothpick to allow the toothpick to easily and effectively pick teeth and effectively probe the gum line. This progressive flexibility feature of the toothpick 16, together with a predetermined longitudinal length of the tip 16b, allows a user to use the tip to safely scrape food or tartar off his or her teeth.

Because the elastomer material of the dental hygiene member 14 is formed over the distal end segment 12a inclusive of the arm 28, the arm provides a perpendicular projection from the distal end segment 12a which anchors the dental hygiene member 14 to the distal end segment. In this regard, the arm 28 prevents the dental hygiene member 14 from slipping off the distal end segment 12a, and further prevents the dental hygiene member form rotating with respect to the distal end segment.

The preferred environment of use of the dental instrument 10 is in association with a toothbrush 34. In this regard, a toothbrush handle has a first portion 36 that connects in a known manner at a proximate end thereof with a brush 38 of known construction. The aforementioned handle 12 now forms a second portion of the toothbrush handle which is integrally connected with the first portion 36 of the toothbrush handle. The first portion 36 of the toothbrush handle is elongated and has a predetermined cross-section S along a transverse axis X' that is oriented perpendicular in relation to the handle axis and to the bristles 38a of the brush 38. The predetermined cross-section S exceeds the cross-section S' of the second portion 12 of the toothbrush handle. Preferably, the second portion 12 of the toothbrush handle extends for approximately one and one-half inches. Preferably further, the indentation resulting from the difference in cross-sections of the first portion 36 of the toothbrush handle and the second portion 12 of the toothbrush handle (that is, S minus S') is approximately equal to the radial length of the trailing side 16c of the toothpick 16. Accordingly, the first portion 36 of the toothbrush handle is usable by a user in a conventional manner for brushing via the brush 38, yet the indentation, characterized by the reduced cross-section of the second portion 12 of the toothbrush handle with respect to the first portion 36 of the toothbrush handle, permits ease of manipulation of the oral hygiene member 14 within the user's mouth. The indentation accommodates the toothpick therewithin, thereby allowing the handle to easily fit through the aperture of a conventional toothpick holder. Further, because the toothpick is located in the space defined by the indentation, toothbrush weight and material cost are minimized, and packaging for the toothbrush can be compact and cost saving.

To those skilled in the art to which this invention appertains, the above described preferred embodiment may be subject to change or modification. Such change or modification can be carried out without departing from the scope of the invention, which is intended to be limited only by the scope of the appended claims.

What is claimed is:

1. A dental instrument, comprising:
   a handle, said handle having a distal end segment, said handle defining a handle axis;
   an arm connected with said distal end segment of said handle, said arm being perpendicularly oriented with respect to said handle axis, said arm having an arm base adjacent said handle and an arm edge remote from said handle, said arm being of planar shape having a taper defined by an arm thickness that varies between a minimum arm thickness at said arm edge to a maximum arm thickness at said arm base, said arm thickness being selected so that said arm is flexible at said arm edge and progressively less flexible toward said arm base;
   an oral hygiene member composed of an elastomer material, said oral hygiene member enveloping said distal end segment of said handle inclusive of said arm, said oral hygiene member comprising:
      a massager comprising a convexly shaped dome having a center of curvature substantially located on said handle axis, said massager further comprising a sidewall oriented parallel with said handle axis, said sidewall integrally connecting with said dome; and
      a toothpick projecting perpendicularly with respect to said handle axis and integrally connected with said sidewall of said massager, said toothpick coincidentally enveloping said arm, said toothpick having a toothpick base adjacent said sidewall and a toothpick tip remote from said sidewall, said toothpick being of planar shape having a taper defined by a toothpick thickness that varies between a minimum toothpick thickness at said toothpick tip to a maximum toothpick thickness at said toothpick base, said toothpick thickness being selected so that said toothpick is flexible at said toothpick tip and progressively less flexible toward said toothpick base, said progressively less flexibility of said toothpick being in part due to said flexibility of said arm acting on said toothpick.

2. The dental instrument of claim 1, wherein said handle has a first cross-section and said distal end segment of said handle has a second cross-section, said second cross-section being less than said first cross-section, wherein an interface between said first and second cross-sections provides an abutment, said elastomer material of said oral hygiene member sealably contacting said abutment.

3. The dental instrument of claim 1, wherein said handle has a proximate end opposite said distal end segment, said proximate end of said handle being provided with a brush, said brush having bristles oriented substantially perpendicular with respect to said handle axis, said handle having a transverse axis perpendicular to said handle axis and said bristles, said handle having a first portion adjacent said brush, said first portion having a first handle cross-section along said transverse axis, said handle having a second portion adjacent said distal end segment, said second portion having a second handle cross-section along said transverse axis, said second handle cross-section being less than said first handle cross-section thereby providing an indentation in said handle, said toothpick being oriented along said transverse axis in said indentation.

4. The dental instrument of claim 1, wherein said planar shape of said arm is substantially similar to said planar shape of said toothpick, wherein said planar shape of said arm is defined by an arm edge having a first longitudinal length, said arm base having a second longitudinal length, and arm trailing side located between said arm edge and said arm base, and an arm leading side located opposite said arm trailing side between said arm edge and said arm base; wherein further, said planar shape of said toothpick is defined by said toothpick tip having a third longitudinal length, said toothpick base having a fourth longitudinal length, a toothpick trailing side located between said toothpick tip and said toothpick base, and a toothpick leading side located opposite said toothpick trailing side between said toothpick tip and said toothpick base; a first distance being defined between said toothpick tip and said toothpick base, a second distance being defined between said arm edge and said arm base, said second distance being substantially sixty percent of said first distance.

5. The dental instrument of claim 4, wherein said handle has a first cross-section and said distal end segment of said handle has a second cross-section, said second cross-section being less than said first cross-section, wherein an interface between said first and second cross-sections provides an abutment, said elastomer material of said oral hygiene member sealably contacting said abutment.

6. The dental instrument of claim 4, wherein said handle has a proximate end opposite said distal end segment, said proximate end of said handle being provided with a brush, said bush having bristles oriented substantially perpendicular with respect to said handle axis, said handle having a transverse axis perpendicular to said handle axis and said bristles, said handle having a first portion adjacent said brush, said first portion having a first handle cross-section along said transverse axis, said handle having a second portion adjacent said distal end segment, said second portion having a second handle cross-section along said transverse axis, said second handle cross-section being less than said first handle cross-section thereby providing an indentation in said handle, said toothpick being oriented along said transverse axis in said indentation.

7. The dental instrument of claim 6, wherein said second handle cross-section is less than said first handle cross-section by a third distance, said first distance being substantially equal to said third distance.

8. The dental instrument of claim 4, wherein said trailing side of said arm and said trailing side of said toothpick are each substantially oriented perpendicular with respect to said handle axis.

9. The dental instrument of claim 8, wherein said leading side of said arm and said leading side of said toothpick are each oriented at a predetermined acute angle with respect to said handle axis.

10. The dental instrument of claim 9, wherein said handle has a first cross-section and said distal end segment of said handle has a second cross-section, said second cross-section being less than said first cross-section, wherein an interface between said first and second cross-sections provides an abutment, said elastomer material of said oral hygiene member sealably contacting said abutment.

11. The dental instrument of claim 10, wherein said handle has a proximate end opposite said distal end segment, said proximate end of said handle being provided with a brush, said bush having bristles oriented substantially perpendicular with respect to said handle axis, said handle having a transverse axis perpendicular to said handle axis and said bristles, said handle having a first portion adjacent said brush, said first portion having a first handle cross-section along said transverse axis, said handle having a second portion adjacent said distal end segment, said second portion having a second handle cross-section along said transverse axis, said second handle cross-section being less than said first handle cross-section thereby providing an indentation in said handle, said toothpick being oriented along said transverse axis in said indentation.

12. The dental instrument of claim 11, wherein said second handle cross-section is less than said first handle cross-section by a third distance, said first distance being substantially equal to said third distance.

13. A toothbrush, comprising:
a handle, said handle having a distal end segment and an opposite proximate end, said handle defining a handle axis;
an arm connected with said distal end segment of said handle, said arm being perpendicularly oriented with respect to said handle axis, said arm having an arm base adjacent said handle and an arm edge remote from said handle, said arm being of planar shape having a taper defined by an arm thickness that varies between a minimum arm thickness at said arm edge to a maximum arm thickness at said arm base, said arm thickness being selected so that said arm is flexible at said arm edge and progressively less flexible toward said arm base;
an oral hygiene member composed of an elastomer material, said oral hygiene member enveloping said distal end segment of said handle inclusive of said arm, said oral hygiene member comprising:
 a massager comprising a convexly shaped dome having a center of curvature substantially located on said handle axis, said massager further comprising a sidewall oriented parallel with said handle axis, said sidewall integrally connecting with said dome; and
 a toothpick projecting perpendicularly with respect to said handle axis and integrally connected with said sidewall of said massager, said toothpick coincidentally enveloping said arm, said toothpick having a toothpick base adjacent said sidewall and a toothpick tip remote from said sidewall, said toothpick being of planar shape having a taper defined by a toothpick thickness that varies between a minimum toothpick thickness at said toothpick tip to a maximum toothpick thickness at said toothpick base, said toothpick thickness being selected so that said toothpick is flexible at said toothpick tip and progressively less flexible toward said toothpick base, said progressively less flexibility of said toothpick being in part due to said flexibility of said arm acting on said toothpick; and
a brush connected with said proximate end of said handle, said brush having bristles oriented substantially perpendicular with respect to said handle axis, said handle having a transverse axis perpendicular to said handle axis and said bristles, said handle having a first portion adjacent said brush, said first portion having a first handle cross-section along said transverse axis, said handle having a second portion adjacent said distal end segment, said second portion having a second handle cross-section along said transverse axis, said second handle cross-section being less than said first handle cross-section thereby providing an indentation in said handle, said toothpick being oriented along said transverse axis in said indentation.

14. The dental instrument of claim 13, wherein said handle has a first cross-section and said distal end segment of said handle has a second cross-section, said second cross-section being less than said first cross-section, wherein an interface between said first and second cross-sections provides an abutment, said elastomer material of said oral hygiene member sealably contacting said abutment.

15. The dental instrument of claim 13, wherein said planar shape of said arm is substantially similar to said planar shape of said toothpick, wherein said planar shape of said arm is defined by an arm edge having a first longitudinal length, said arm base having a second longitudinal length, and arm trailing side located between said arm edge and said arm base, and an arm leading side located opposite said arm trailing side between said arm edge and said arm base; wherein further, said planar shape of said toothpick is defined by said toothpick tip having a third longitudinal length, said toothpick base having a fourth longitudinal length, a toothpick trailing side located between said toothpick tip and said toothpick base, and a toothpick leading side located opposite said toothpick trailing side between said toothpick tip and said toothpick base; a first distance being defined between said toothpick tip and said toothpick base, a second distance being defined between said arm edge and said arm base, said second distance being substantially sixty percent of said first distance.

16. The dental instrument of claim 15, wherein said second handle cross-section is less than said first handle cross-section by a third distance, said first distance being substantially equal to said third distance.

17. The dental instrument of claim 16, wherein said handle has a first cross-section and said distal end segment of said handle has a second cross-section, said second cross-section being less than said first cross-section, wherein an interface between said first and second cross-sections provides an abutment, said elastomer material of said oral hygiene member sealably contacting said abutment.

18. The dental instrument of claim 17, wherein said trailing side of said arm and said trailing side of said toothpick are each substantially oriented perpendicular with respect to said handle axis.

19. The dental instrument of claim 18, wherein said leading side of said arm and said leading side of said toothpick are each oriented at a predetermined acute angle with respect to said handle axis.

* * * * *

UNITED STATES PATENT AND TRADEMARK OFFICE
CERTIFICATE OF CORRECTION

PATENT NO. : 5,323,795
DATED : June 28, 1994
INVENTOR(S) : Mathew G. Berens

It is certified that error appears in the above-indentified patent and that said Letters Patent is hereby corrected as shown below:

In the Abstract at line 25 thereof, after "conventional" delete "toothpick" and insert therefor —toothbrush—.

At Column 5, line 66 thereof, after "ventional" delete "toothpick" and insert therefor —toothbrush—.

Signed and Sealed this

Sixth Day of September, 1994

Attest:

BRUCE LEHMAN

*Attesting Officer*  *Commissioner of Patents and Trademarks*